United States Patent [19]

Bennett

[11] Patent Number: Plant 6,787

[45] Date of Patent: May 9, 1989

[54] MINIATURE ROSE PLANT, NAMED 'HERBIE'

[75] Inventor: Cecilia L. D. Bennett, Chula Vista, Calif.

[73] Assignee: Susan M. O'Brien, Chula Vista, Calif.

[21] Appl. No.: 151,252

[22] Filed: Feb. 1, 1988

[51] Int. Cl.[4] ..... A01H 5/00

[52] U.S. Cl. ..... Plt./9

[58] Field of Search ..... Plt./9

*Primary Examiner*—James R. Feyrer

[57] ABSTRACT

The subject of the present disclosure is a new and distinct variety of miniature rose plant, named 'Herbie', which is characterized by its mauve blooms, ranging from near Rhodamine Purple to near Peony Purple with a deeper mauve margin of the same colors. The blooms are usually borne one to a stem with hybrid tea form but on occasion may be produced in sprays of 3 to 5 blooms or more. The bush is vigorous, well-branched and produces moderate to heavy quantity of blooms.

1 Drawing Sheet

The present invention relates to a new and distinct variety of a hardy, dwarf, bush plant of the miniature class; the variety being primarily characterized as a mauve.

The variety is further characterized by:

Long stemmed blooms of hybrid tea-type form, borne usually one to a stem but on occasion in sprays of 3 to 5 or more. The blooms are held very erect and well above the foliage.

It has a slight fragrance.

The plant ranges in height from 24 to 36 inches (approximately 60 to 90 cm). The canes are sturdy and erect with moderate branching and medium to heavy foliage covering. The plant is a moderate to heavy bloomer that does well either in the greenhouse or outdoors.

The plant has good growth habits, well-shaped and attractive, bearing numerous leaflets of average size.

I have found this variety to be easily reproduced from cuttings.

The seed parent was Deep Purple (floribunda, mauve; R. Kordes; introduced by Armstrong Nursery, 1980), and the pollen parent was Dilly Dilly (miniature, mauve; Cecilia Bennett; introduced by Tiny Petals Nursery, 1985). It differs from its seed parent in the following way. It is a miniature rose, and Deep Purple is a floribunda. It differs from its pollen parent in the following way. It is an average size miniature rose (35 to 45 mm when fully opened), and Dilly Dilly is a larger then average miniature rose (50 mm or more in diameter when fully opened) and appropriately larger foliage.

The descriptive matter which follows pertains to roses grown and color values observed in plants and newly opened blooms in the months of March through August 1986. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Herbie', the following is a detailed description thereof in outline; all major color plate identifications being by reference to the British Colour Council Horticultural Colour Chart, except where common terms of color definition are employed.

Type: Hardy, spreading and upright, bushy, greenhouse or outdoor, decorative or exhibition potted plant.

Class: Miniature.

Variety name: 'Herbie'.

Flowers Borne: Usually one to a stem, but occasionally in sprays of 3 to 5 or more on erect stems with foliage well below the blooms.

Quantity of blooms: Moderate to heavy both outdoors or greenhouse grown.

Bud:

*Peduncle.*—Variable in length (30 to 40 mm); average diameter and sturdy; ranging in color from near Scheeles Green (860/1 to 860 page 860) to near Lettuce Green (861/1 to 861 page 861) with some tinting of bronze.

*Hairs.*—Extremely small and numerous with a reddish color; located over the entire surface of the peduncle and sepals, but not present on the calyx tube.

*Opening.*—Opens well in all weather.

Bloom:

*Size when fully opened.* —Average for a miniature variety (35 to 45 mm).

Petalage.—Double; averaging 25 to 30 petals, arranged regularly, plus petaloids (3 to 5 or more).

*Form.*—Urn-shaped to ovoid as the bloom progresses. The petals remain somewhat cupped with the apex and/or margins reflexed outward, becoming at maturity more loosely cupped; and the petals reflex more tightly (quilling), until each row of petals forms a five-pointed star.

Petals: Fairly thick with good substance; both the upper and under surfaces of all petals have a matte finish.

*Shape.*—Outer petals are of a broad obovate form. The intermediate petals are very much like the outer petals only narrower. The inner petals are a broad lanceolate form; and the petaloids are also lanceolate form with some occasional irregularities.

Color: Newly opened flowers from plants grown outdoors (March through August 1986), Chula Vista, Calif.

*Outside petals.*—Upper Surface — Ranging from near Rhodamine Purple (29/3 to 29/2 page 29)

to near Peony Purple (729/3 to 729/2 page 729) with a darker margin of near Rhodamine Purple (29/1 to 29 page 29) to near Peony Purple (729/1 to 729 page 729). Under Surface — Same Colors as upper surface.

*Intermediate and inner petals.*—Same color as outer petals but without the darker margins.

*General color effect.*—Newly opened flowers — Rich mauve with outer petals deep mauve at the margins. Three days open — Some fading of the color. Five to seven days — Some additional fading of the color, but it remains mauve throughout the life of the bloom.

*Flower longevity.*—(March through August 1986) Plant in pot 3 to 5 days from bud with sepals reflexed to fully opened bloom. Holding at fully opened with gradual fading of color for 3 to 5 days or longer. Cut bloom at living room temperature 5 to 7 days or longer.

Reproductive organs:

*Stamens.*—A generous amount arranged uniformly around the pistil.

*Filaments.*—Varying in length with shorter filaments more proximal to the pistil; golden yellow including the anthers.

*Pollen.*—Abundant.

*Pistil.*—Long, abundant and spreading; pale yellow at the base to reddish at the top with pale yellow caps on the styles.

*Ovaries.*—All encased in calyx.

*Hips.*—Some.

*Seeds.*—3 to 5 or more in each hip.

*Sepals.*—Permanent; spear-shaped; open as the bloom opens, recurving against the peduncle, when the bloom is fully opened.

Foliage:

*Leaves.*—Five to seven leaflets on the average; medium size for a miniature rose plant.

*Leaflets.*—Broad ovate-shaped.

*Margin.*—Very serrated with tinting of bronze, especially noticeable on the newer foliage.

*Color.*—Ranging from near Spinach Green (0960/2 to 0960/1 page 0960) to near Fern Green (0862/1 to 0862 page 0862) with occasional bronzing of the margins, especially noticeable on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has a few if any hairs but does contain 3 to 5 small thorns.

*Stipules.*—Varying in length from small to medium; average width; tapering auricles angled outward at about 45 degrees.

Growth:

*Habit.*—Upright and spreading; average to tall height for a miniature rose plant.

*Growth.*—Vigorous and well-branched.

*Canes.*—Medium diameter; sturdy; held erect.

*Main stems.*—Color — Ranging from near Spinach Green (0960/3 to 0960/2 page 0960) to near Fern Green (0862/3 to 0862/2 page 0862) with occasional tiniting of bronze, especially on the newer stems.

*Thorns.*—Averaging 10 to 12 per 10 cm on the main stems and fewer on the branches. Reddish in color; small to average size; slender and straight.

*Branches.*—Same color as the main stems.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant, named 'Herbie' of hardy, dwarf, vigorous growth, well-branched and attractive in appearance, substantially as illustrated and described; it is further characterized by its blooms of rich mauve, ranging from near Rhodamine Purple to near Peony Purple with a deeper mauve of the same color on the margin of the outer petals; and, the blooms are hybrid tea form and are usually borne one to a stem but on occasion may come in sprays of 3 to 5 or more.

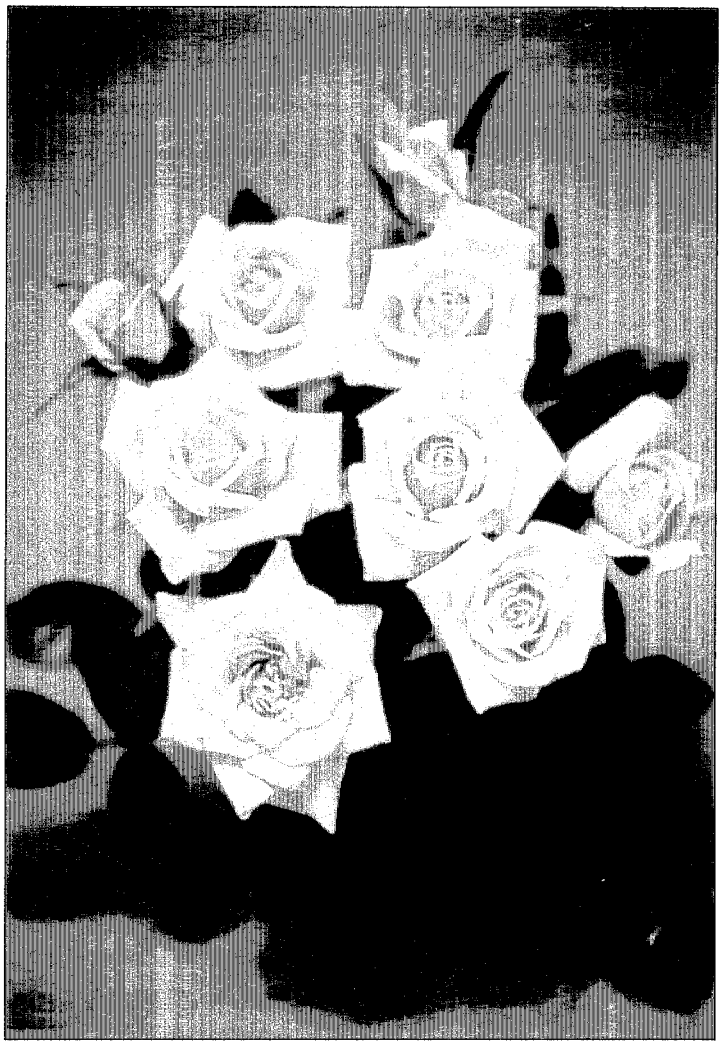

* * * * *